United States Patent
Quinn

(10) Patent No.: US 7,997,275 B2
(45) Date of Patent: Aug. 16, 2011

(54) COUGH CATCHER WITH PROTECTION AGAINST GERM TRANSMISSION BY HAND CONTACT

(76) Inventor: Michael Quinn, Doaktown (CA)

( * ) Notice: Subject to any disclaimer, the term of this patent is extended or adjusted under 35 U.S.C. 154(b) by 456 days.

(21) Appl. No.: 12/292,188

(22) Filed: Nov. 13, 2008

(65) Prior Publication Data

US 2009/0145445 A1   Jun. 11, 2009

Related U.S. Application Data

(60) Provisional application No. 60/996,771, filed on Dec. 5, 2007.

(51) Int. Cl.
| A61F 6/06 | (2006.01) |
| A61B 19/00 | (2006.01) |
| B63C 11/16 | (2006.01) |
| A62B 18/08 | (2006.01) |
| A62B 17/04 | (2006.01) |
| A62B 7/10 | (2006.01) |
| A62B 18/02 | (2006.01) |
| A62B 18/10 | (2006.01) |
| A62B 9/02 | (2006.01) |

(52) U.S. Cl. ............. 128/836; 128/201.13; 128/201.11; 128/201.23; 128/201.25; 128/201.26; 128/205.25; 128/205.27; 128/205.29; 128/206.29; 128/206.12; 128/206.15; 128/206.21; 128/207.12; 128/205.24; 128/863

(58) Field of Classification Search ............. 128/201.13, 128/201.11, 201.23, 201.25, 201.26, 205.25, 128/205.27, 205.29, 206.29, 206.12, 206.15, 128/206.21, 207.12, 205.24, 836, 863
See application file for complete search history.

(56) References Cited

U.S. PATENT DOCUMENTS

| 2,572,547 A | 10/1951 | Webb |
| 3,027,896 A | 4/1962 | Newton |
| 3,276,445 A | 10/1966 | Langdon |
| 3,719,188 A | 3/1973 | Fisher et al. |
| 4,328,797 A | 5/1982 | Rollins, III et al. |
| 4,643,182 A | 2/1987 | Klein |
| 4,792,013 A | 12/1988 | Boynton |
| 4,856,509 A | 8/1989 | Lemelson |
| 4,883,052 A | 11/1989 | Weiss |
| 5,117,821 A | 6/1992 | White |
| 5,269,294 A | 12/1993 | Rogozinski |
| 5,413,094 A | 5/1995 | McBrearty |
| 5,697,105 A | 12/1997 | White |
| 6,085,864 A | 7/2000 | Copeland et al. |
| 6,584,976 B2 | 7/2003 | Japuntich et al. |

(Continued)

FOREIGN PATENT DOCUMENTS

CA    614142    2/1961

(Continued)

*Primary Examiner* — Patricia M Bianco
*Assistant Examiner* — Nihir Patel

(57) ABSTRACT

In order to prevent tainting of a cougher's hand with germs, the product from a cough is carried in contact with a germicide inside a hollow article, and is vented out of the hollow article, in directions away from the user's face and hand holding the article. More specifically, the cough catcher has a hollow region for accepting the product from a cough therein. This hollow region has a filter element containing a germicide mounted therein, and a series of channels formed between the filter element and a bottom surface of the hollow region. The channels communicate with vent ports around a rim portion of the cough catcher. The vent ports are oriented away from both the mouth opening and the outside surface of the cough catcher for conveying the product from a cough away from both the face and the hand of a user.

17 Claims, 5 Drawing Sheets

U.S. PATENT DOCUMENTS

| | | |
|---|---|---|
| 6,986,348 B2 | 1/2006 | Carter |
| 7,152,600 B2 | 12/2006 | Freriks et al. |
| 2004/0055605 A1 | 3/2004 | Griesbach, III |
| 2005/0034722 A1 | 2/2005 | Carter |
| 2005/0045186 A1 | 3/2005 | Takowsky |
| 2005/0194010 A1 | 9/2005 | Sankot |
| 2006/0130845 A1 | 6/2006 | Schegerin |
| 2006/0254591 A1 | 11/2006 | Marx |

FOREIGN PATENT DOCUMENTS

| | | |
|---|---|---|
| CA | 1280851 | 3/1991 |
| CA | 2390222 | 5/2001 |
| WO | WO2007053816 | 5/2007 |

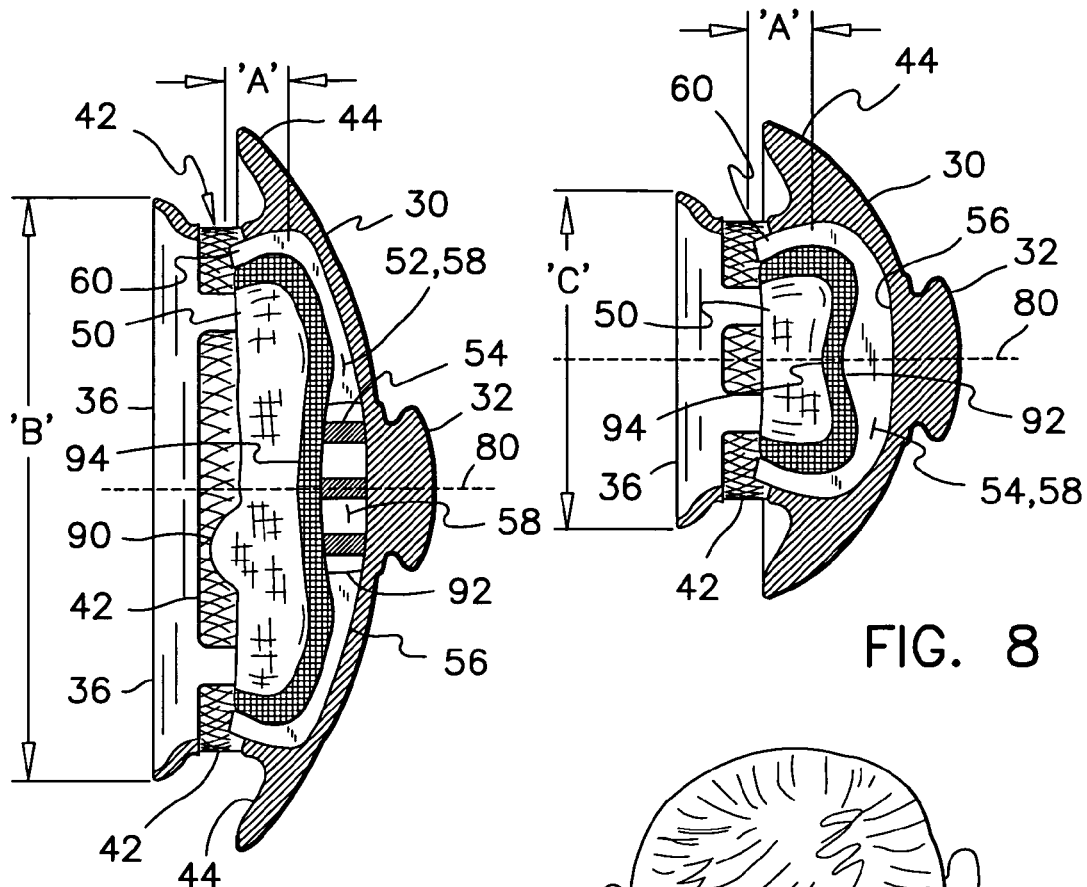
FIG. 7
FIG. 8
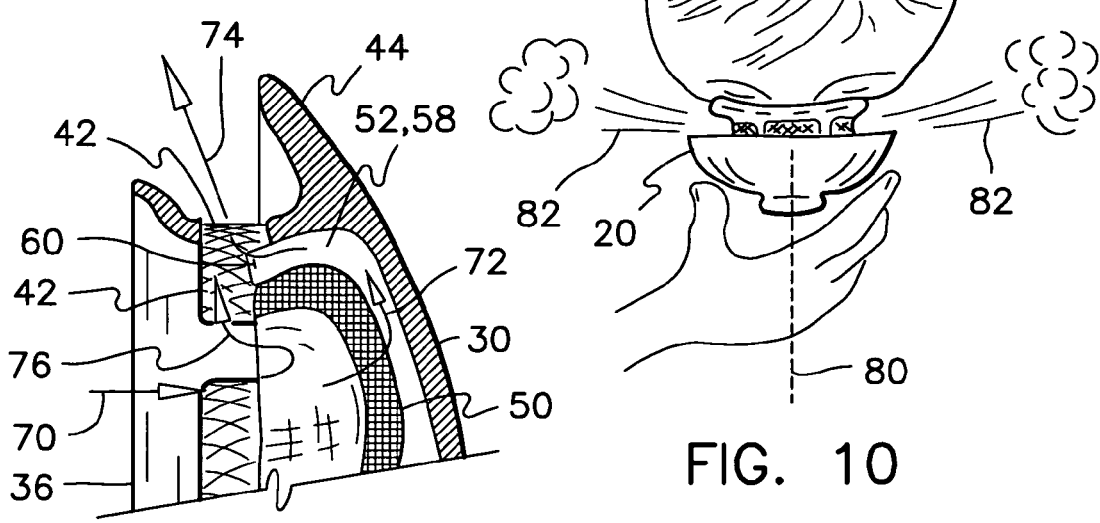
FIG. 9
FIG. 10

COUGH CATCHER WITH PROTECTION AGAINST GERM TRANSMISSION BY HAND CONTACT

This application claims the benefit of U.S. Provisional Application No. 60/996,771 filed Dec. 5, 2007.

FIELD OF THE INVENTION

This invention pertains to cough catchers, and more particularly, it pertains to a cough catcher having a germicide therein and air flow paths to divert the product from a cough or a sneeze away from the user's hand.

BACKGROUND OF THE INVENTION

Health authorities from around the world tell us to cover our mouth and nose when we cough or sneeze, to prevent the spread of diseases. The spread of germs has been a major concern to the medical profession since the outbreak of several cases of the Severe Acute Respiratory Syndrome (SARS) around the world during the winter of 2003. Since that time, World Health Organization has been on the alert for a possible pandemic. Several governments, health organizations and institutions in many countries are now promoting a Cover-Your-Cough™ campaign in all establishments under their authorities, and a Ask-for-a-Mask® campaign in hospitals and other health care facilities.

Health authorities tell the public to cover their cough with a tissue, with the hand or by coughing in one's sleeve at the crook of the arm. If a cough or a sneeze is covered by the hand or a tissue, thorough washing of the hands is recommended before touching others, or touching surfaces which others will touch, of before preparing or serving food to others. This is often impractical for care givers, cooks, waiters, cashiers, hairdressers, flight attendants, travelers, sales people, and other people working with people.

The solution offered by continuously wearing a mask is also impractical. Although both the surgical and the dust masks currently available have the capability to filter out germs, these masks are made to filter air in a normal breathing-type air flow. These masks are not appropriate to accept the outburst of air that is generated by a cough or a sneeze, due to the fact that the flow of air in a cough can reach 100 mph. Also, the permanent mounting of a surgical or a dust mask over one's face is a deterrent for use by those whose coughing is limited to occasional instances per day for example.

The prior art offers at least two examples of cough catchers that are held to one's face only when coughing or sneezing. These cough catchers are described in the following documents.

U.S. Patent Application by P. W. Sankot, published on Sep. 8, 2005 under the USPTO Publication No. US 2005/0194010. This document discloses a disposable cone-like device which may include a bulb-like protrusion at its apex that may enclose an absorbent fibrous material for absorbing fluids and particulate that may be forcefully expelled from the user. The device may also include an opening in the bulb-like protrusion that allows the user to lock one or more fingers there through to securely grasp the device.

U.S. Patent Application by Davis Marx, published on Nov. 16, 2006 under the USPTO Publication No. US 2006/0254591. This document also discloses a cone-like mask having an opening at its apex for releasing excess air during a cough. A filter covers that opening. The filter portion forms a bulb-like protrusion that is held in one's hand during use.

Although the concept of holding a cough catcher to one's mouth only when coughing is more practical than wearing a surgical mask all the time, the articles of the prior art have only limited protection against the spreading of germs to the user's hand holding the cough catcher. It is believed that there is a possibility that fluid and particulate from a cough can pass through the filter or through the absorbent material in the devices of the prior art and contaminate the user's hand. Therefore, the spread of diseases using the articles of the prior art is only partly checked.

For these reasons, it is believed that a need exists for a better cough catcher that can be held in one's hand and used only when needed, and that is capable of absorbing and disinfecting the product from a cough while preventing the tainting of the user's hands with germ-containing fluid, particulate or mist.

SUMMARY OF THE INVENTION

In the present invention, however, there is provided a cough catcher that is held by hand to the user's mouth, or nose and mouth, only when needed. The cough catcher has a disinfectant therein and vent ports oriented for deflecting the outburst of a cough away form both the face and the hand of a user. The person using the cough catcher can swiftly cover a cough or a sneeze by holding the cough catcher to his/her face by hand, and safely resume his/her normal function without worries of infecting others.

Broadly described, a first aspect of the present invention consists of a method for treating the product from a cough for preventing tainting the hand of a cougher with germs. This method comprises the steps of; passing the product from a cough in contact with a germicide inside a hollow article, and venting the product from a cough out of the hollow article, in directions away from the user's mouth and hand holding the article.

In another aspect of the present invention, there is provided a cough catcher having an outside surface, a mouth opening, a rim portion between the outside surface and the mouth opening. The cough catcher has a hollow region therein between the rim portion, the mouth opening and the outside surface, for accepting the product from a cough therein. This hollow region has a bottom surface; a filter element mounted therein, and a series of channels formed between the filter element and the bottom surface for supporting the filter element at a distance from the bottom surface. The cough catcher also has vent ports around the rim portion for venting the product from a cough outside the hollow region.

The channels communicate with the vent ports. The vent ports are oriented away from both the mouth opening and the outside surface of the cough catcher, for conveying the product from a cough away from both the face and the hand of a user.

In yet another aspect of the cough catcher of the present invention, the outside surface has larger circumference than the rim. The portion of the outside surface overhanging the rim provides a deflector near the vent ports for further deflecting the product from a cough away from the hand of the user.

In a further aspect of the present invention, the cough catcher has an oval-shaped mouth opening. The proportion of the major axis over the minor axis of the mouth opening is a same value as a ratio of the height over width of a person's face portion between the eyes and the chin. The cough catcher can therefore be used to cover the mouth and nose of a user, or the mouth only, according to the preference of the user.

This brief summary has been provided so that the nature of the invention may be understood quickly. A more complete understanding of the invention can be obtained by reference to the following detailed description of a preferred embodiment thereof in connection with the attached drawings.

BRIEF DESCRIPTION OF THE DRAWINGS

A preferred embodiment of the present invention is illustrated in the accompanying drawings, in which like numerals denote like parts throughout the several views, and in which:

FIG. 7 is a longitudinal cross section view through the cough catcher as seen along line 7-7 in FIG. 3;

FIG. 8 is a transverse cross-section view through the cough catcher as seen along line 8-8 in FIG. 6;

FIG. 9 is an enlarged view of the upper portion of the longitudinal cross-section view of FIG. 7;

FIG. 10 is a top view of the cough catcher in use by a user;

DESCRIPTION OF THE PREFERRED EMBODIMENT

Figure 1:
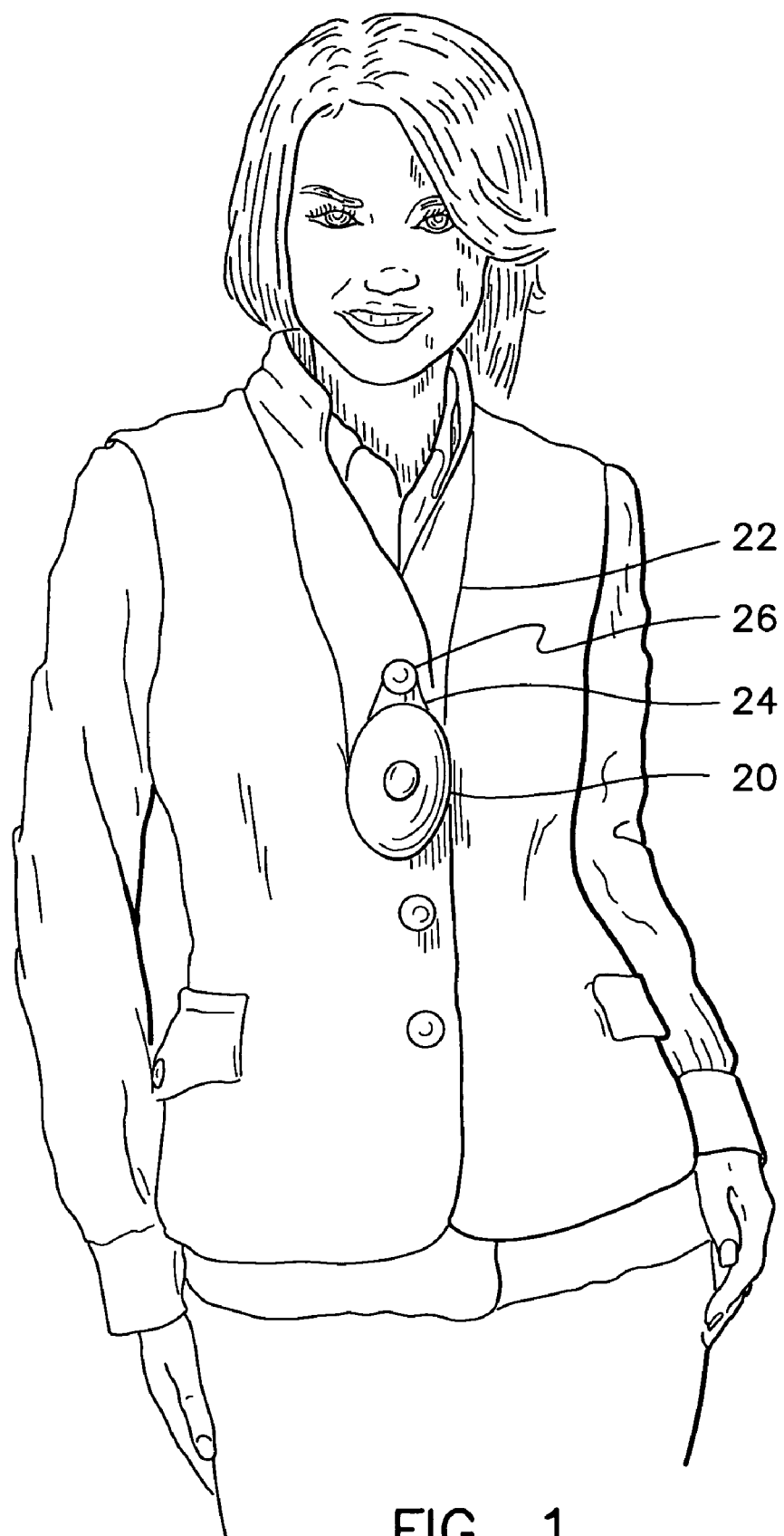
FIG. 1 represents a flight attendant wearing a cough catcher according to the preferred embodiment of the present invention, as a pendant.
Figure 2:
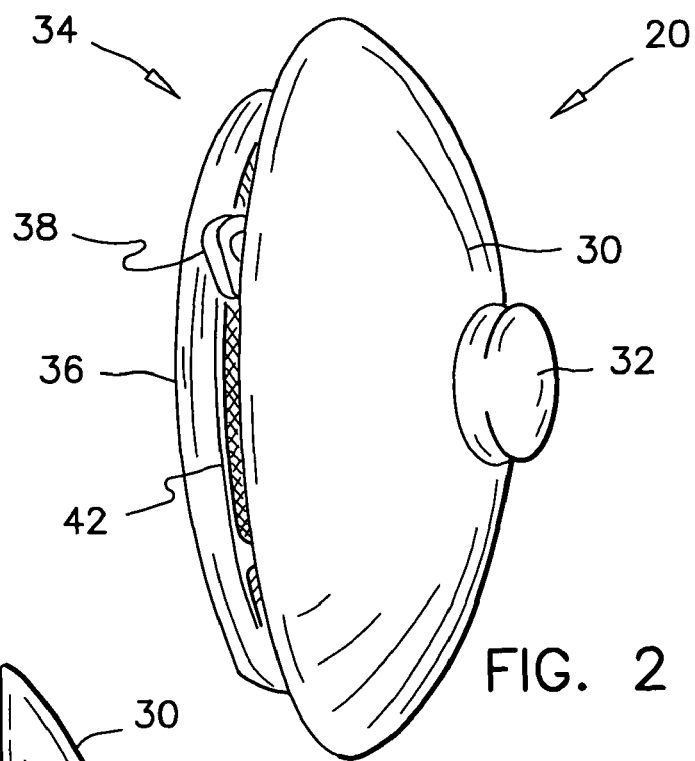
FIG. 2 is a perspective front and left side view of the preferred cough catcher.
Figure 4:
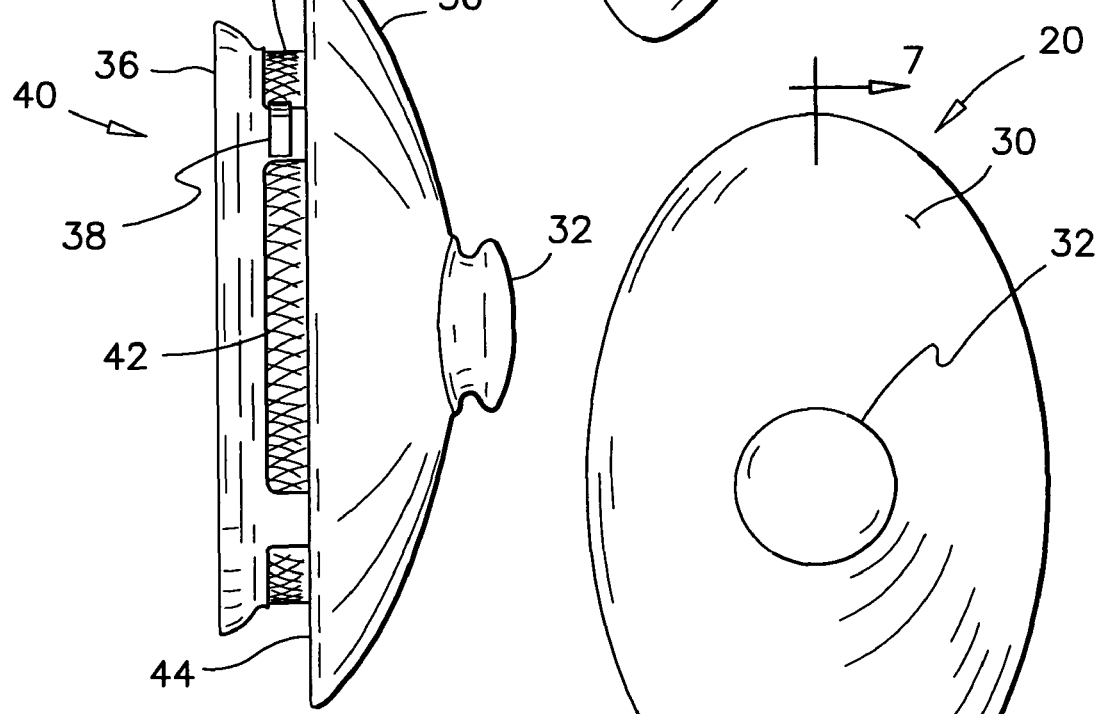
FIG. 4 is a left side view of the preferred cough catcher.
Figure 3:
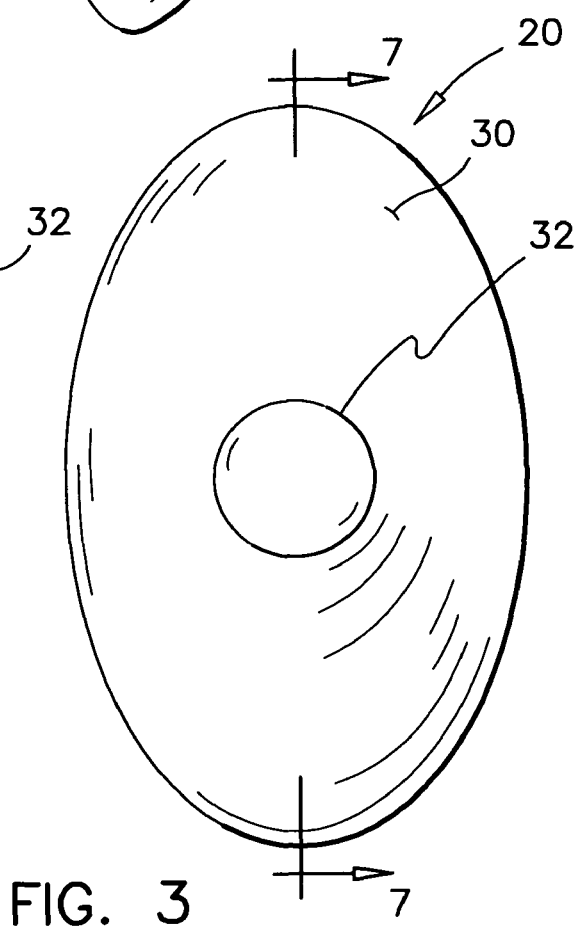
FIG. 3, is a front view of the preferred cough catcher.

Referring to FIG. 1, the preferred cough catcher 20 has an oval and convex front surface and is preferably carried as a pendant so that it is readily available to a user to cover a cough or a sneeze. The preferred cough catcher 20 has a neck string 22 thereon that is sufficiently long to hold the cough catcher against a user's chest. The cough catcher 20 also has an elastic button cord 24 that is shorter than the neck string, and that is used to retain the cough catcher to a button 26 on the user's costume for example. When the elastic button cord 24 is hung to a button 26, the cough catcher 20 does not dangle away from the user's chest when the user leans forward to tend to a client, as in the case of a flight attendant, a waitress or a nurse for example.

The preferred cough catcher 20 has a colour that is selected to match users' uniforms, when it is used by people of a same organization for example. It can also be used to display an emblem or a written message.

Referring now to FIGS. 2-6, the general features of the preferred cough catcher 20 will be explained. The cough catcher 20 has a convex front surface 30. The convex shape of the front surface is optional. A protruding knob 32 is centered on that surface. The knob 32 is also optional.

The cough catcher 20 is made of a flexible, impermeable material, such as rubber or malleable plastic for example. It preferably has an oval shape, although a circular shape can also be used. The cough catcher 20 has a front surface 30 that has a larger circumference than the rim portion 34 thereof, such that it overhangs the rim portion 34.

A pair of eyelets 38 are provided along the surface of the rim portion 34, to retain the neck string 22, or both the neck string 22 and the button cord 24. The length of the elastic button cord 24 is selected such that it retains the position as shown by label 24' when it is in a relaxed position. When the elastic button cord 24 is in a relaxed position, off a button, it does not hinder the user of the cough catcher 20 when the cough catcher 20 is handled quickly to the user's face.

The rim portion 34 of the cough catcher 20 has a malleable lip 36 thereon defining a mouth opening 40.

The rim portion 34 of the cough catcher 20 also has a number of vent ports 42 located therein, around the entire circumference thereof. The vent ports 42 are located between the lip 36 and the overhang 44 of the front surface 30. These vent ports 42 communicate with the hollow region of the cough catcher 20 and are used to release the product from a cough or a sneeze from the cough catcher 20 during use.

The hollow region of the cough catcher 20 contains a filter element 50 and longitudinal and transverse ribs labelled as 52 and 54 respectively. These ribs have a certain depth for supporting the filter element 50 off the bottom surface 56 of the hollow region. The filter element 50 has filtering and absorbing capacities and is impregnated with a germicide. It can be manufactured in a paper-like or a fabric-like material.

For reference purposes, the hollow region of the cough catcher 20 is that region defined between the lip 36, the bottom surface 56, and the vent ports 42, as illustrated in FIG. 7.

Figures 5, 6:
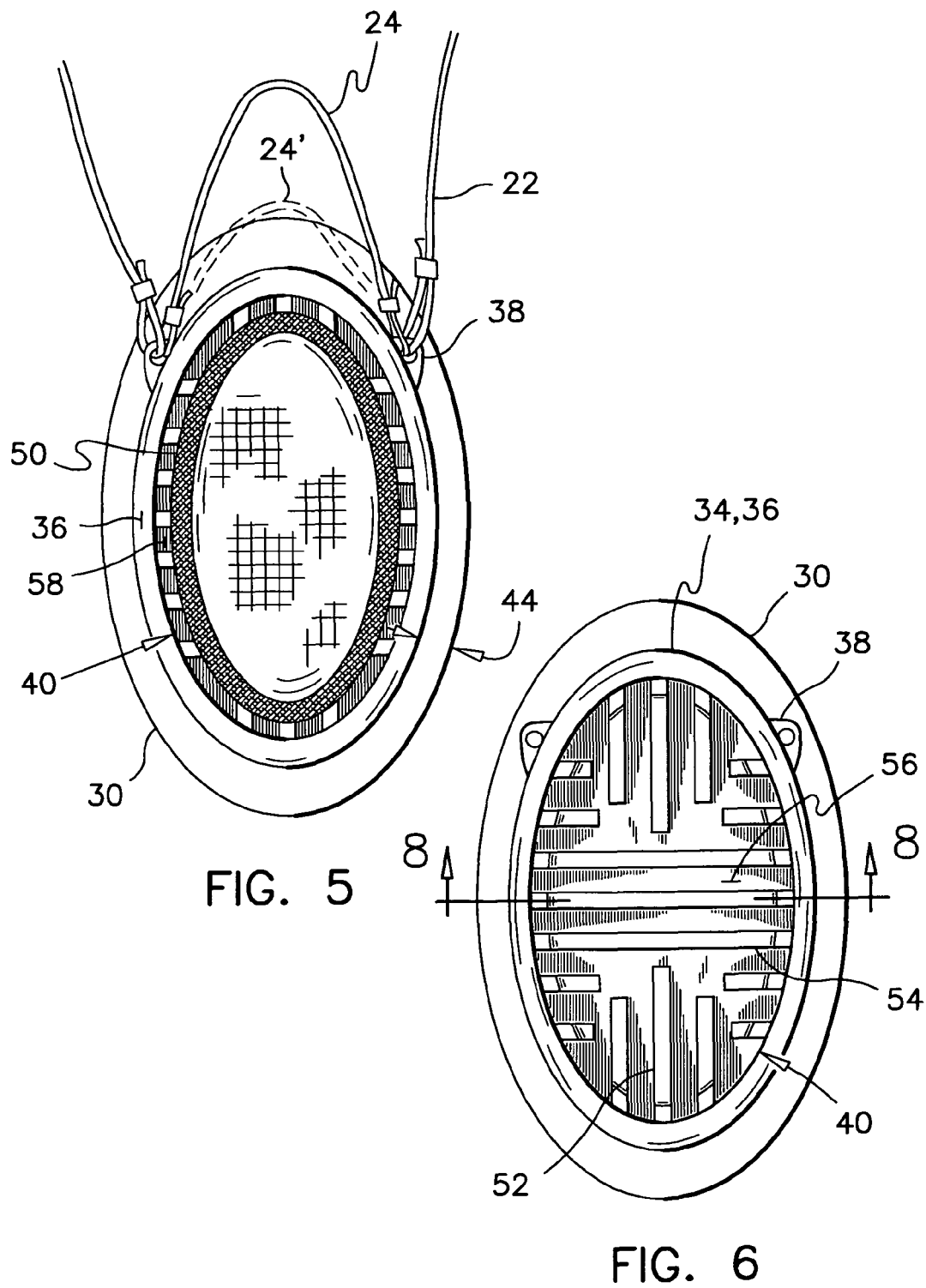
FIG. 5 is a rear view of the preferred cough catcher.
FIG. 6 is also a rear view of the preferred cough catcher as seen without the filter element therein.

Referring now to FIGS. 7-9 while still looking at FIGS. 5 and 6, the functions of the ribs 52, 54 will be explained in greater details. The ribs 52, 54 support the filter element 50 off the bottom surface 56 of the hollow region and define a series of channels 58 between the filter element 50 and the bottom surface 56 of the hollow region. The end 60 of each channel 58 communicates with one of the vent ports 42, as it is better illustrated in FIG. 9.

In use, the outburst of air and moist material from a cough as represented by arrow 70 in FIG. 9, is directed inside the cough catcher 20 and against the filter element 50. Some particles may pass through the filter element 50 as indicated by arrow 72 and are carried by the pressure of the cough inside one of the channels 58 and toward one of the vent ports 42 as represented by arrow 74. Some particles may bounce against the filter element 50 as represented by arrow 76 and are also forced toward one of the vent ports 42 by the pressure of the cough.

The vent ports 42 are oriented sideways from a direction of a cough, so that a flow of air there through is oriented at substantially a right angle from an axis 80 extending between the center of the mouth opening 40 and the center of the outside convex surface 30 when the cough catcher is used, as illustrated in FIG. 10. Axis 80 is also referred to herein as the axis of a cough. The air surge from a cough is thereby vented away from both the face and the hand of the user of the cough catcher 20, as represented by lines 82 in FIG. 10.

It will be appreciated that the overhang portion 44 of the front surface 30 constitutes a deflector to further deflect cough particles away from the user's hand, and to further shield the user's hand from germs that may still be present in the air vented out from the cough catcher 20.

Referring back to FIGS. 7 and 8, the ribs 52, 54 define a diverging region "A" at the beginning of the hollow portion of the cough catcher 20. The purpose of this diverging region "A" is to retain the filter element 50 inside the cough catcher without fasteners. The resiliency of the filter element 50 and the pressure that this resiliency generates along the diverting region holds the filter against the ribs 52, 54. A tab 90 as illustrated in FIG. 7, may also be provided to assist the user in the replacement of a filter element 50.

Both the longitudinal ribs 52 and the transverse ribs 54 have a high region 92 over the bottom surface 56 of the hollow region of the cough catcher, for bending the filter element 50 and for forming a convex curvature 94 in the filter element 50 over the bottom surface 56. This convex curvature 94 contributes to diverting the product from a cough toward the sides of the filter element 50 to better absorb the product. This convex surface 94 also contributes to diverting the product from a cough toward the vent ports 42.

Figure 11:
FIG. 11 is a front view of the preferred cough catcher being used to cover the mouth and nose of a user.
Figure 12:
FIG. 12 is a front view of the preferred cough catcher being used to cover the mouth only of the user.

Furthermore, the preferred cough catcher 20 has an oval-shaped mouth opening 40 with a longitudinal dimension 'B' along its major axis that is sufficient to cover both the mouth and nose of a user, as illustrated in FIG. 11. The opening 40 has a transverse dimension 'C' along its minor axis that is made to cover the mouth only of a user, such as illustrated in FIG. 12. The ratio of the dimension 'B' over 'C' is the same as the height over width of a person's face portion between the eyes and the chin. The preferred cough catcher 20 can thereby be used with the major axis oriented vertically or horizontally, according to the choice of the user. Preferred dimensions for a model of cough catcher for use by adults would be five inches along the dimension 'B' and three inches along the dimension "C".

What is claimed is:

1. A cough catcher having an outside surface, a mouth opening, a rim portion between said outside surface and said mouth opening, and a hollow region, between said rim portion, said mouth opening and said outside surface, for accepting a product from a cough therein;

said hollow region having a bottom surface; a filter element mounted therein, and a series of channels formed therein between said filter element and said bottom surface for supporting said filter element at a distance from said bottom surface; each of said channels being oriented away from said filter element for guiding away from said filter element said product from said cough passing through said filter element;

said rim portion having vent ports there around for venting said product from said cough outside said hollow region; said vent ports communicating with said channels;

said vent ports being oriented away from both said mouth opening and said outside surface.

2. The cough catcher as claimed in claim 1 wherein said filter element is impregnated with a disinfectant.

3. The cough catcher as claimed in claim 1 wherein said vent ports are oriented at a right angle from an axis extending between a center of said outside surface and a center of said mouth opening.

4. The cough catcher as claimed in claim 1 wherein said mouth opening has an oval outline having dimensions to enclose both a mouth and nose of a user.

5. The cough catcher as claimed in claim 1, wherein said channels define a diverging region inside said hollow region, and said filter element has resiliency and is removably held to said channels by pressure thereof against said channels along said diverging region.

6. The cough catcher as claimed in claim 1, further comprising a neck string attached thereto.

7. The cough catcher as claimed in claim 6, further comprising an elastic button cord attached thereto, said cord being shorter than said neck string.

8. The cough catcher as claimed in claim 6, further comprising a handle on said outside surface.

9. The cough catcher as claimed in claim 1, wherein said outside surface has a convex and oval shape.

10. The cough catcher as claimed in claim 9, being made of a malleable impermeable material.

11. The cough catcher as claimed in claim 10, wherein said outside convex surface has larger circumference than said rim portion, and has a deflector overhanging said rim portion along the entire circumference of said rim portion.

12. The cough catcher as claimed in claim 11, wherein said deflector has a surface for deflecting the product from said cough away from said outside convex surface.

13. The cough catcher as claimed in claim 12, wherein said vent ports extend around a circumference of said rim portion.

14. The cough catcher as claimed in claim 1, wherein said filter element has a convex curvature along said bottom surface.

15. A cough catcher having an outside convex surface, a mouth opening, a rim portion between said outside convex surface and said mouth opening, and a hollow region therein for accepting a product from a cough;

said hollow region having a bottom surface; a filter element mounted therein, and a series of channels formed therein between said filter element and said bottom surface for supporting said filter element away from said bottom surface, each of said channels being oriented away from said filter element for guiding away from said filter element said product from said cough passing through said filter element;

said channels defining a diverging region inside said hollow region, and said filter element being held to said channels by said diverging region;

vent ports around said rim portion for venting said product of said cough outside said hollow region, said vent ports communicating with said channels;

said vent ports being oriented at a right angle from an axis extending between a center of said outside convex surface and a center of said mouth opening;

said outside convex surface having larger circumference than said rim portion, and a deflector overhanging said rim; said deflector having surfaces for deflecting said product from said cough away from said outside convex surface;

said outside convex surface having an oval shape and a handle formed thereon.

16. The cough catcher as claimed in claim 15, wherein said mouth opening has an oval outline having dimensions to enclose both a mouth and a nose of a user.

17. The cough catcher as claimed in claim 15, wherein said filter element has a disinfectant impregnated therein.

* * * * *